(12) United States Patent
Burnett et al.

(10) Patent No.: US 10,814,030 B1
(45) Date of Patent: Oct. 27, 2020

(54) HYBRID FULL SPECTRUM AIR PURIFIER DEVICES, SYSTEMS, AND METHODS

(71) Applicant: Dust Free, LP, Royce City, TX (US)

(72) Inventors: Gregg W. Burnett, Royse City, TX (US); Joshua Pulis, Rockwall, TX (US)

(73) Assignee: DUST FREE, LP, Royce City, TX (US)

( * ) Notice: Subject to any disclaimer, the term of this patent is extended or adjusted under 35 U.S.C. 154(b) by 305 days.

(21) Appl. No.: 15/947,335

(22) Filed: Apr. 6, 2018

(51) Int. Cl.
*A61L 9/20* (2006.01)
*B01D 53/88* (2006.01)
*F24F 3/16* (2006.01)

(52) U.S. Cl.
CPC ............ *A61L 9/205* (2013.01); *B01D 53/885* (2013.01); *F24F 3/1603* (2013.01); *A61L 2209/14* (2013.01); *A61L 2209/16* (2013.01); *B01D 2255/2073* (2013.01); *B01D 2255/20707* (2013.01); *B01D 2255/802* (2013.01);
(Continued)

(58) Field of Classification Search
CPC .. A61L 9/205; A61L 2209/14; A61L 2209/16; F24F 3/1603; F24F 2003/1667; F24F 2003/1682; B01D 53/885; B01D 2279/50; B01D 2259/804; B01D 2255/802; B01D 2257/91; B01D 2255/20707; B01D 2255/2073
See application file for complete search history.

(56) References Cited

U.S. PATENT DOCUMENTS

| 2,881,854 A | 4/1959 | Uehre |
| 4,859,329 A | 8/1989 | Fink |

(Continued)

FOREIGN PATENT DOCUMENTS

| CN | 2392106 Y | 8/2000 |
| CN | 2922905 Y | 7/2007 |

(Continued)

OTHER PUBLICATIONS

"Curve" American Heritage Dictionary of the English Language, 2011, 1 page, Fifth Edition, Houghton Mifflin Harcourt Publishing Company.
(Continued)

*Primary Examiner* — Regina M Yoo
(74) *Attorney, Agent, or Firm* — Fogarty LLP (57) ABSTRACT

A hybrid full-spectrum air purification device employs a UV light source; ionization, both negative and positive or only negative ions; and, adsorbent VOC filters, zeolite, potassium permanganates, carbon, polymers, tris(hydroxymethyl)aminomethane, tromethamine, and/or the like, applied to carbon monolith structures. Room temperature bi-metallic nano-particle catalysts, such as supported noble metal based catalysts (e.g. platinum, palladium, gold, silver, etc.) with inert oxide in this case platinized tin oxide (Pt/SnOx) combined with, or without, non-noble metal oxides such as manganese dioxide ($MnO_2$) and/or titanium dioxide ($TiO_2$), and/or the like, may also be applied to the carbon monolith(s). The device is suitable for installation immediately above, or adjacent, a cooling coil with the air flow entering the germicidal (UV) area first, followed by the VOC catalyst filters and finally being exposed to the dual/single polarity ionization zone.

20 Claims, 7 Drawing Sheets

(52) U.S. Cl.
CPC .... *B01D 2257/91* (2013.01); *B01D 2259/804* (2013.01); *B01D 2279/50* (2013.01); *F24F 2003/1667* (2013.01); *F24F 2003/1682* (2013.01)

(56) References Cited

U.S. PATENT DOCUMENTS

| | | | |
|---|---|---|---|
| 5,011,609 | A | 4/1991 | Fink |
| 5,120,435 | A | 6/1992 | Fink |
| 5,236,585 | A | 8/1993 | Fink |
| 5,523,057 | A | 6/1996 | Mazzilli |
| 5,578,113 | A | 11/1996 | Glenn |
| 5,919,422 | A | 7/1999 | Yamanaka et al. |
| 6,221,314 | B1 | 4/2001 | Bigelow |
| 6,315,963 | B1 | 11/2001 | Speer |
| 6,546,883 | B1 | 4/2003 | Fink et al. |
| 6,730,265 | B2 | 5/2004 | Horton, III |
| 6,752,970 | B2 | 6/2004 | Schwartz et al. |
| 6,784,440 | B2 | 8/2004 | Fink et al. |
| 6,849,107 | B1 | 2/2005 | Huffman |
| 6,949,228 | B2 | 9/2005 | Ou Yang et al. |
| 6,997,185 | B2 | 2/2006 | Han et al. |
| 7,160,566 | B2 | 1/2007 | Fink et al. |
| 7,635,659 | B2 | 12/2009 | Naganuma et al. |
| 7,871,518 | B2 | 1/2011 | Ellis et al. |
| 7,988,923 | B2 | 8/2011 | Fink et al. |
| 8,168,122 | B2 | 5/2012 | Lee |
| 8,658,101 | B1 | 2/2014 | Burnett |
| 8,926,899 | B1 | 1/2015 | Burnett |
| 8,932,533 | B2 | 1/2015 | Kruglick |
| 9,066,988 | B1 | 6/2015 | Burnett |
| 9,205,169 | B1 | 12/2015 | Burnett |
| 9,782,510 | B1 | 10/2017 | Burnett |
| 2001/0046461 | A1 | 11/2001 | Hamilton |
| 2003/0077211 | A1 | 4/2003 | Schwartz et al. |
| 2003/0150708 | A1 | 8/2003 | Fink |
| 2003/0230477 | A1 | 12/2003 | Fink et al. |
| 2004/0016887 | A1 | 1/2004 | Fink et al. |
| 2004/0056201 | A1 | 5/2004 | Fink et al. |
| 2004/0156959 | A1 | 8/2004 | Fink et al. |
| 2004/0166037 | A1 | 8/2004 | Youdell et al. |
| 2004/0170537 | A1 | 9/2004 | Hara |
| 2004/0197243 | A1 | 10/2004 | Schwartz et al. |
| 2004/0226813 | A1 | 11/2004 | Wang |
| 2005/0163653 | A1 | 7/2005 | Crawford et al. |
| 2005/0186124 | A1 | 8/2005 | Fink et al. |
| 2005/0238551 | A1 | 10/2005 | Snyder et al. |
| 2006/0144690 | A1 | 7/2006 | Fink et al. |
| 2006/0163135 | A1 | 7/2006 | Ellis et al. |
| 2006/0201119 | A1 | 9/2006 | Song |
| 2006/0228275 | A1 | 10/2006 | Rutman et al. |
| 2006/0266221 | A1 | 11/2006 | Fink et al. |
| 2007/0000407 | A1 | 1/2007 | Leong |
| 2007/0107597 | A1 | 5/2007 | Cheung |
| 2007/0110860 | A1 | 5/2007 | Fink et al. |
| 2007/0243114 | A1 | 10/2007 | Morrow et al. |
| 2008/0093210 | A1 | 4/2008 | Edwards |
| 2009/0041617 | A1 | 2/2009 | Lee |
| 2009/0183943 | A1 | 7/2009 | Leistner et al. |
| 2009/0217690 | A1 | 9/2009 | Silderhuis |
| 2010/0120347 | A1 | 5/2010 | Gehring et al. |
| 2010/0196223 | A1* | 8/2010 | Hay ............... A61L 9/205 422/186 |
| 2011/0033346 | A1 | 2/2011 | Bohlen et al. |
| 2011/0250125 | A1 | 10/2011 | Fink et al. |
| 2012/0199005 | A1 | 8/2012 | Koji et al. |
| 2013/0146783 | A1 | 6/2013 | Boodaghians et al. |
| 2014/0017135 | A1 | 1/2014 | Boodaghians et al. |
| 2015/0064061 | A1 | 3/2015 | Taghipour |
| 2015/0224218 | A1 | 8/2015 | Burnett |
| 2015/0306271 | A1* | 10/2015 | Willette ............ B01D 53/04 422/119 |
| 2016/0250372 | A1 | 9/2016 | Dytrych et al. |

FOREIGN PATENT DOCUMENTS

| | | |
|---|---|---|
| CN | 101245939 A | 8/2008 |
| CN | 201135626 Y | 10/2008 |
| DE | 20211178 U1 | 10/2002 |
| JP | 2004-663 A | 1/2004 |
| WO | 2006/134149 A1 | 12/2006 |
| WO | 2014/003446 A1 | 1/2014 |

OTHER PUBLICATIONS

Vincent, "Answered: Can you describe a square with 1 equation?", Mar. 1, 2010, 5 pages.
"Cylinder", 2010, 1 page, Random House Kenerman Webster's College Dictionary.

\* cited by examiner

HYBRID FULL SPECTRUM AIR PURIFIER DEVICES, SYSTEMS, AND METHODS

TECHNICAL FIELD

This specification relates generally to air treatment and purification, and, more particularly, to devices, systems and methods for providing hybrid full-spectrum air treatment and purification.

BACKGROUND

Air treatment devices such as air filters and purifiers are designed to remove or reduce the number of contaminants from the air. These devices may be manufactured either as stand-alone units or as part of air handler units (AHU), heating, ventilation, and air conditioning (HVAC) systems, ventilation ducts, etc.

For example, a typical air treatment device may reduce odors, air pollutants, smoke, mold, bacteria, and viruses. In some cases, such devices may be installed or mounted into air conditioning and heating systems air ducts where most air quality problems start. When an HVAC system is in operation, an air treatment device may oxidize pollutants, breaking them down into hydro-peroxides, super oxide ions, hydroxide ions, and/or other friendlier substances.

A typical HVAC system is used to maintain indoor air quality; however, the primary function of most HVAC systems is to control the temperature and humidity of the air. Many indoor air pollutants, such as volatile organic compounds (VOCs), cannot be removed by typical HVAC systems.

Ultraviolet (UV) light can be used in HVAC systems to significantly reduce the number of microbials in ductwork and air space, which helps to reduce possible health problems associated with inhaling microbials. UV light is also beneficial in keeping HVAC coils free of mold, which increases system efficiency. Hence, an air cleaning device may often be added to a HVAC system to remove VOCs. A photocatalytic air cleaning device in an HVAC system typically comprises a UV lamp that illuminates a photocatalytic filter to create free radicals that reduce VOCs. Photocatalytic air cleaning devices are a common technique for indoor air purification and deodorization.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention is directed to systems and methods which provide hybrid full-spectrum air purification that brings hybrid VOC adsorbent technology, room temperature catalysts, ultra-violet light, and ionization together into a format suitable for installation as a conduit device, in an air duct, or the like. A hybrid full-spectrum air purification device employs a UV light source; ionization (e.g., forming both negative and positive ions or negative ions only); and adsorbent VOC filters, such as zeolite, potassium permanganates, carbon, polymers, tris(hydroxymethyl)aminomethane (Tris), tromethamine (Tham), or the like, applied to a carbon monolith structure. Room temperature bi-metallic nano-particle catalysts, such as supported noble metal based catalysts (e.g. platinum (Pt), palladium (Pd), gold (Au), silver (Ag), etc.) with inert oxide in this case platinized tin oxide (Pt/SnOx) combined with, or without, non-noble metal oxides such as manganese dioxide (MnO2) and/or titanium dioxide (TiO2), and/or the like, may also be applied to the carbon monolith structure. The device is suitable for installation immediately above, or adjacent, a cooling coil with the air flow entering the germicidal (UV) area first, followed by the VOC catalyst filter and/or carbon monolith structure, and finally being exposed to the dual/single polarity ionization zone.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Having thus described the invention in general terms, reference will now be made to the accompanying drawings, which are not necessarily drawn to scale and which are incorporated in and form part of the specification and in which like numerals designate like parts, illustrate embodiments of the present invention and together with the description explain the principles of the invention. In the drawings:

While this specification provides several embodiments and illustrative drawings, a person of ordinary skill in the art will recognize that the present specification is not limited only to the embodiments or drawings described. It should be understood that the drawings and detailed description are not intended to limit the specification to the particular form disclosed, but, on the contrary, the intention is to cover all modifications, equivalents and alternatives falling within the spirit and scope of the invention. Also, any headings used herein are for organizational purposes only and are not intended to limit the scope of the description. As used herein, the word "may" is meant to convey a permissive sense (i.e., meaning "having the potential to"), rather than a mandatory sense (i.e., meaning "must"). Similarly, the words "include," "including," and "includes" mean "including, but not limited to."

DETAILED DESCRIPTION

The foregoing has outlined rather broadly the features of some present embodiments in order that the detailed description that follows may be better understood. Additional features and advantages will be described hereinafter which form the subject of the claims of the invention. It should be appreciated that the conception and specific embodiments disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

Some embodiments now will be described more fully hereinafter with reference to the accompanying drawings. Some embodiments may, however, take many different forms and should not be construed as limited to the embodiments set forth herein. Rather, these embodiments are provided so that this disclosure will be thorough and complete and will fully convey the scope of the invention to those skilled in the art. A person of ordinary skill in the art will be able to use the various embodiments of the invention.

Embodiments described below are described in the context of stand-alone hybrid full-spectrum air purification devices and/or hybrid full-spectrum air purification systems or methods deployed in other HVAC systems, air filtration devices, air treatment systems, or the like. The hybrid full-spectrum air purifier device brings hybrid VOC adsorbent technology, room temperature catalysts, ultra-violet light, and ionization together into a format suitable for installation in a conduit device adapted for deployment in the air stream of a HVAC air duct, in conjunction with exchanger coils, other HVAC installations, air filtration devices, air treatment systems, and/or the like.

Figure 1:
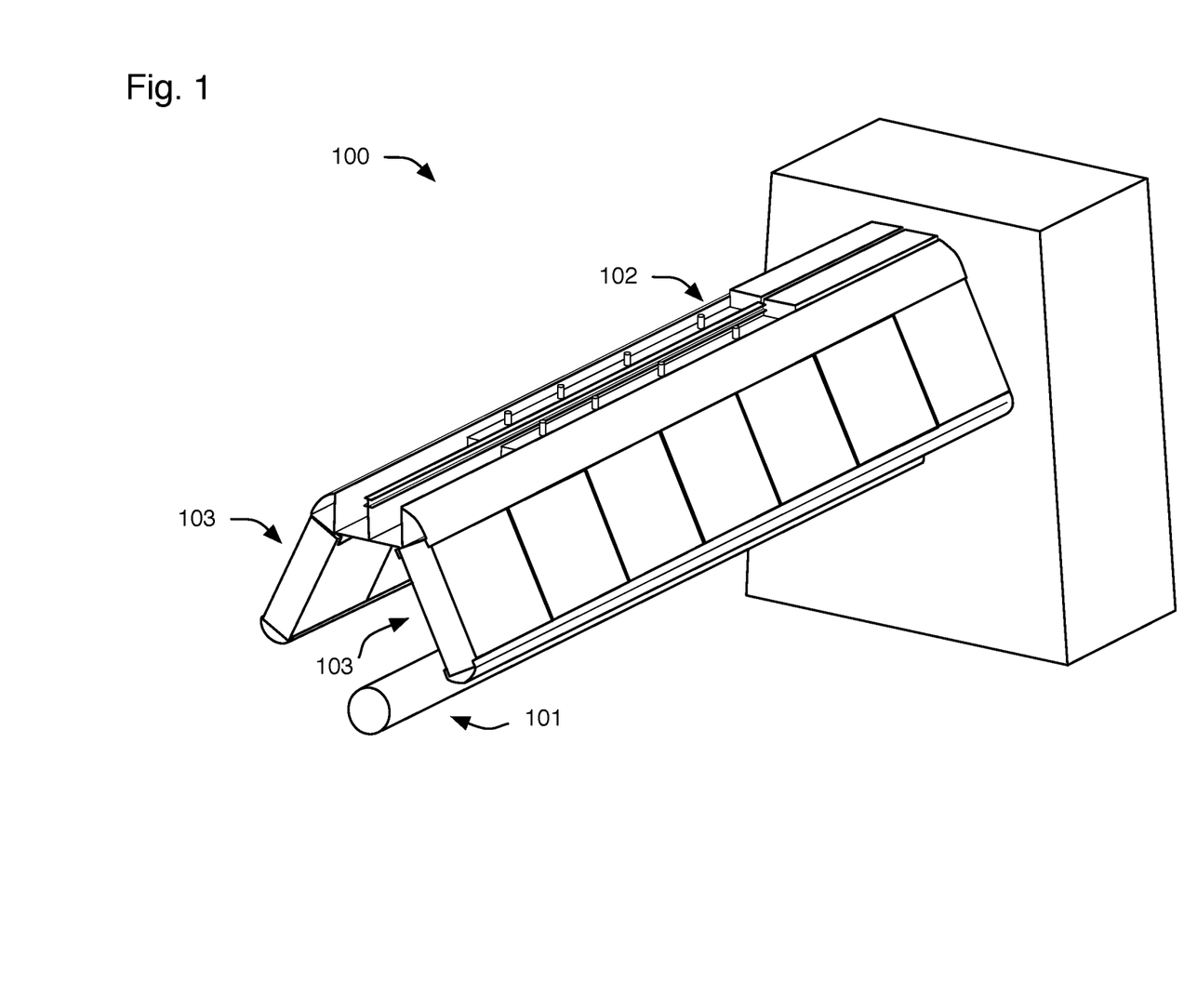
FIG. 1 is a perspective view of an example hybrid full-spectrum air purification device according to some embodiments.

FIG. 1 is a perspective view of example hybrid full-spectrum air purification device 100 according to some embodiments. Embodiments of the hybrid full-spectrum air purifier device include UV light source 101, which may be any ultraviolet light source, including one or more florescent UV light sources (e.g., florescent UV light tubes), one or more UV Light Emitting Diode (LED) arrays, or the like. Using LEDs as a UV light source may achieve some advantages. First, it is generally thought that LEDs consume less power than comparable non-LED light sources. Further, LEDs generally have a longer life expectancy than comparable non-LED light sources. These advantages can allow devices to operate with lower costs. Additionally, with the relatively narrow wavelength bands of LEDs, a UV LED lamp configuration can include only those LEDs with specific bands of wavelength that are effective for the purposes described herein while avoiding some bands of wavelengths.

Embodiments of the hybrid full-spectrum air purifier device of the present systems and methods for air purification and/or treatment may also include ionization, both negative and positive ionization, or only negative ions. Such ionization may be provided by at least one ionizer or ion generator 102 disposed in conjunction with the present photocatalytic device to provide ions within a housing or structure of the photocatalytic device and/or in the HVAC conduit or coil housing in which the device is deployed. Air circulated therethrough carries the ions out and oppositely charged ions are neutralized. Such an ionizer may be of the "needle-type," wherein a high voltage is applied to a needle to produce ions, and/or the ionizer may be of a "carbon fiber-based type," wherein the high voltage is applied to a carbon fiber mat or set of filaments or bristles to produce ions. The ionizer may thus generate negative and/or positive ions using the relatively high voltage to ionize air molecules, such as through needlepoint ionization, or the like.

Embodiments of the hybrid full-spectrum air purifier device employ adsorbent VOC filters 103, such as zeolite, potassium permanganates, carbon, polymers, tris(hydroxymethyl)aminomethane (Tris), tromethamine (Tham), or the like, applied to a carbon monolith structure. The carbon monolith structure is an extruded substrate. A carbon monolith consists of many parallel channels separated by thin walls that are coated with the catalytic active substance. The channels may be round or polygonal (e.g., square, hexagonal, etc.). Preferably, due to a high open frontal area (the open spaces in the cross-sectional area) pressure loss of air flowing through the structure is low. The adsorbents may be used to capture molecular-sized pollutants, odors, and non-particulates and to remove VOCs in air passing through or over the carbon monoliths. Room temperature bi-metallic nanoparticle catalysts may additionally, or alternatively, be applied to the carbon monolith structure, including supported noble metal based catalysts (e.g. platinum (Pt), palladium (Pd), gold (Au), silver (Ag), etc.) with inert oxide, for example, platinized tin oxide (Pt/SnOx) combined with, or without, non-noble metal oxides, such as manganese dioxide ($MnO_2$) and/or titanium dioxide ($TiO_2$).

Hence, embodiments of the hybrid full-spectrum air purifier device employ a heretofore novel and proprietary combination of the technologies describe above. The hybrid full-spectrum air purifier device maximizes reduction in particulate, VOC, and microbial levels of air passing through a central air system or other housing in which the device is deployed. That is, the hybrid full-spectrum air purifier device deploys this unique mix of technologies to work in concert to extend the life of the catalysts, keep the production costs of the catalysts within reason (supported noble metals are expensive), provide a level of germicidal treatment to the surfaces in the air handler along with the moving air, and provide charged ions into the air flow to conglomerate fine, respirable dust particles that are easier for mechanical filters to capture.

Embodiments of the present hybrid full-spectrum air purifier device of the present systems and methods for air purification and/or treatment can be deployed in many configurations. For example, attention is directed to co-owned, co-pending U.S. patent application Ser. No. 15/075,438, filed Mar. 23, 2016, entitled Photocatalytic Device with Light Emitting Diodes(LEDs), which is incorporated herein by reference, shows various configurations into which embodiments of the present device may be incorporated. In such configurations, the present device may be deployed in place of the UV light source, substrates, etc.

Figure 2:
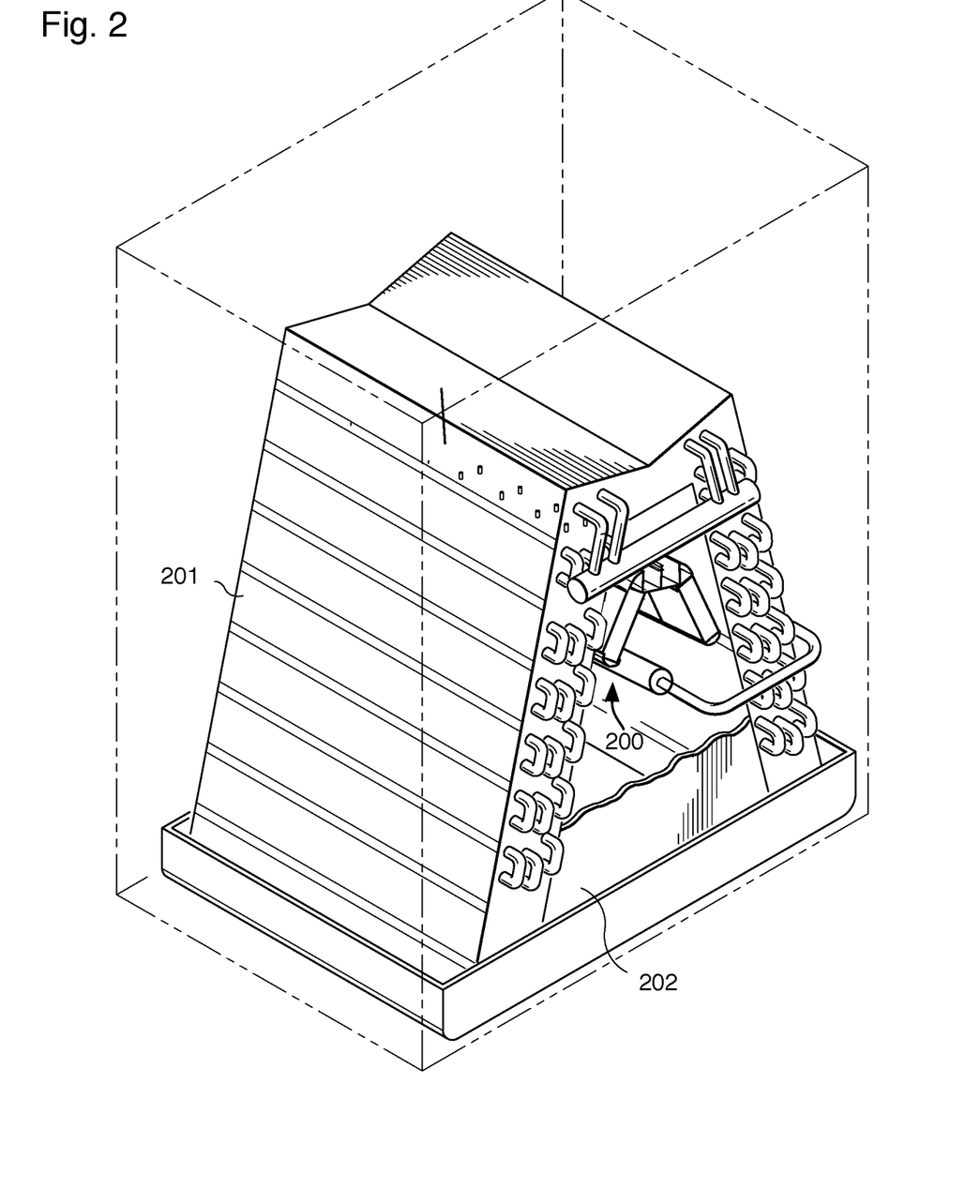
FIG. 2 is a perspective view of an example embodiment of a hybrid full-spectrum air purification device deployed in conjunction with a HVAC evaporator coil according to some embodiments.

For example, the hybrid full-spectrum air purifier device may be installed immediately above or adjacent to a cooling coil, wherein the air flow enters the UV germicidal area first, followed by the VOC catalyst carbon monolith filters and finally being exposed to the dual/single polarity ionization zone. FIG. 2 is a perspective view of example hybrid full-spectrum air purification device 200 deployed in conjunction with an HVAC evaporator coil, wherein the hybrid full-spectrum air purification device 200 is mounted inside evaporator coil (or A-Coil) 201 in an air conditioning system. Hybrid full-spectrum air purification device 200 may be mounted on a delta plate 202 on the side of A-Coil 201 or similarly deployed to remove VOCs as the device cleans the coil 201 and reduces bioaerosols.

Figure 3:
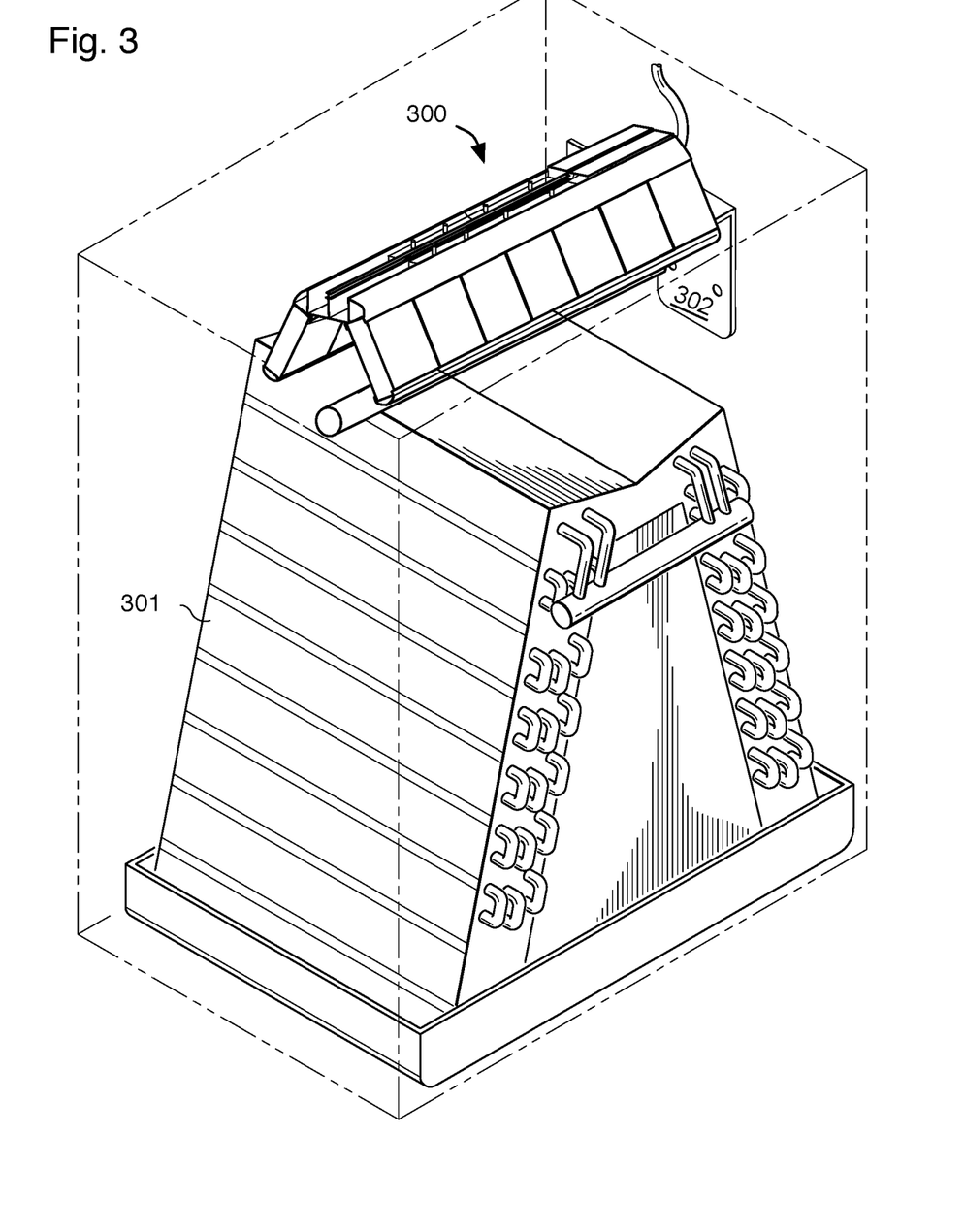
FIG. 3 is another perspective view of an example embodiment of a hybrid full-spectrum air purification device deployed in conjunction with a HVAC evaporator coil in another configuration according to some embodiments.

FIG. 3 is another perspective view of a hybrid full-spectrum air purification device 300 that is deployed in conjunction with HVAC evaporator coil 301 in another configuration. Hybrid full-spectrum air purification device 300 is mounted above A-Coil 301 in an air conditioning system. Hybrid full-spectrum air purification device 300 may be mounted on a duct 302 or other enclosure housing A-Coil 301 to remove VOCs as the device cleans the coil 301 and reduces bioaerosols.

Figure 4:
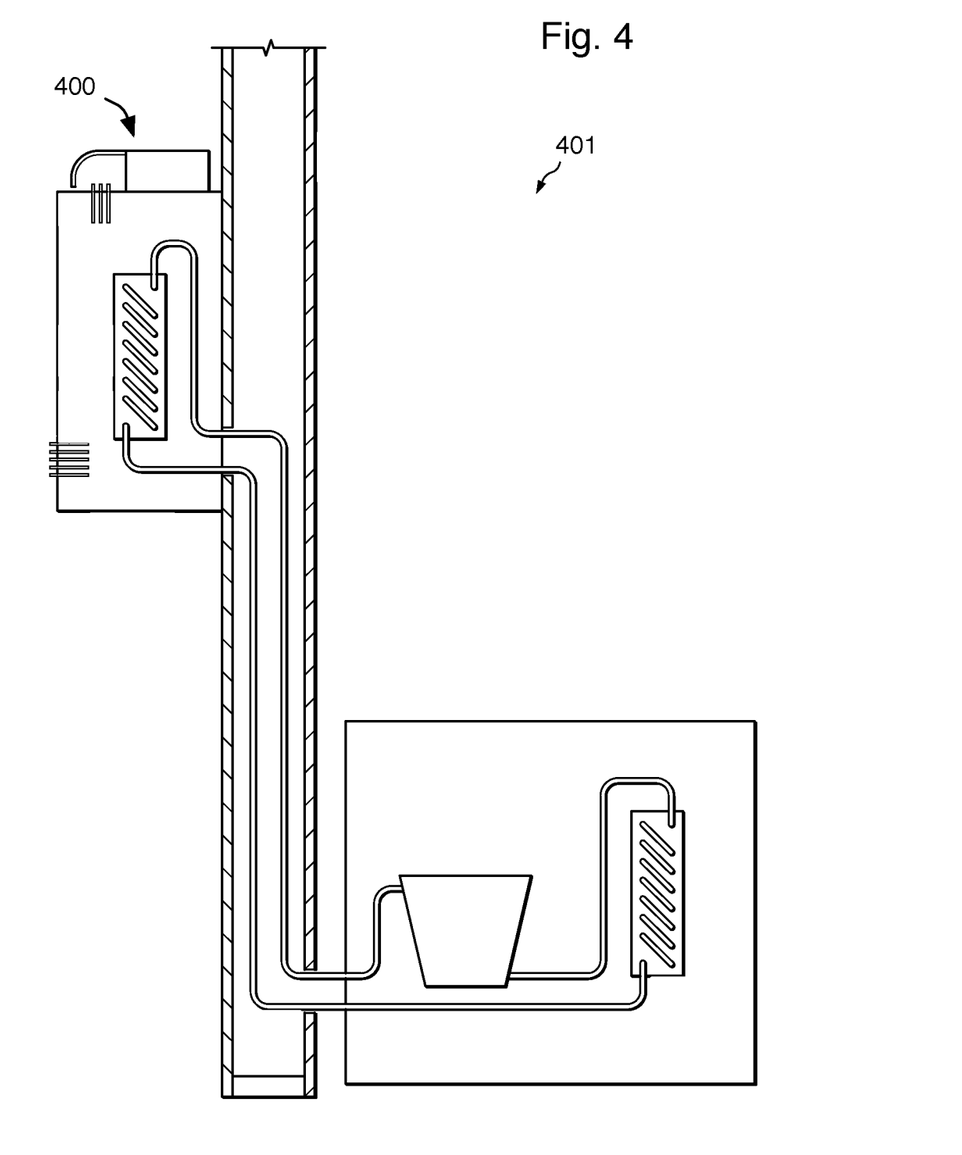
FIG. 4 diagrammatically illustrates a mini-split heating and cooling system with which a hybrid full-spectrum air purifier is deployed according to some embodiments.

In relation to other examples, FIG. 4 diagrammatically illustrates a mini-split heating and cooling system 401 in which a hybrid full-spectrum air purifier 400 is deployed at an outlet of mini-split heating and cooling system 401 according to some embodiments.

Figure 5:
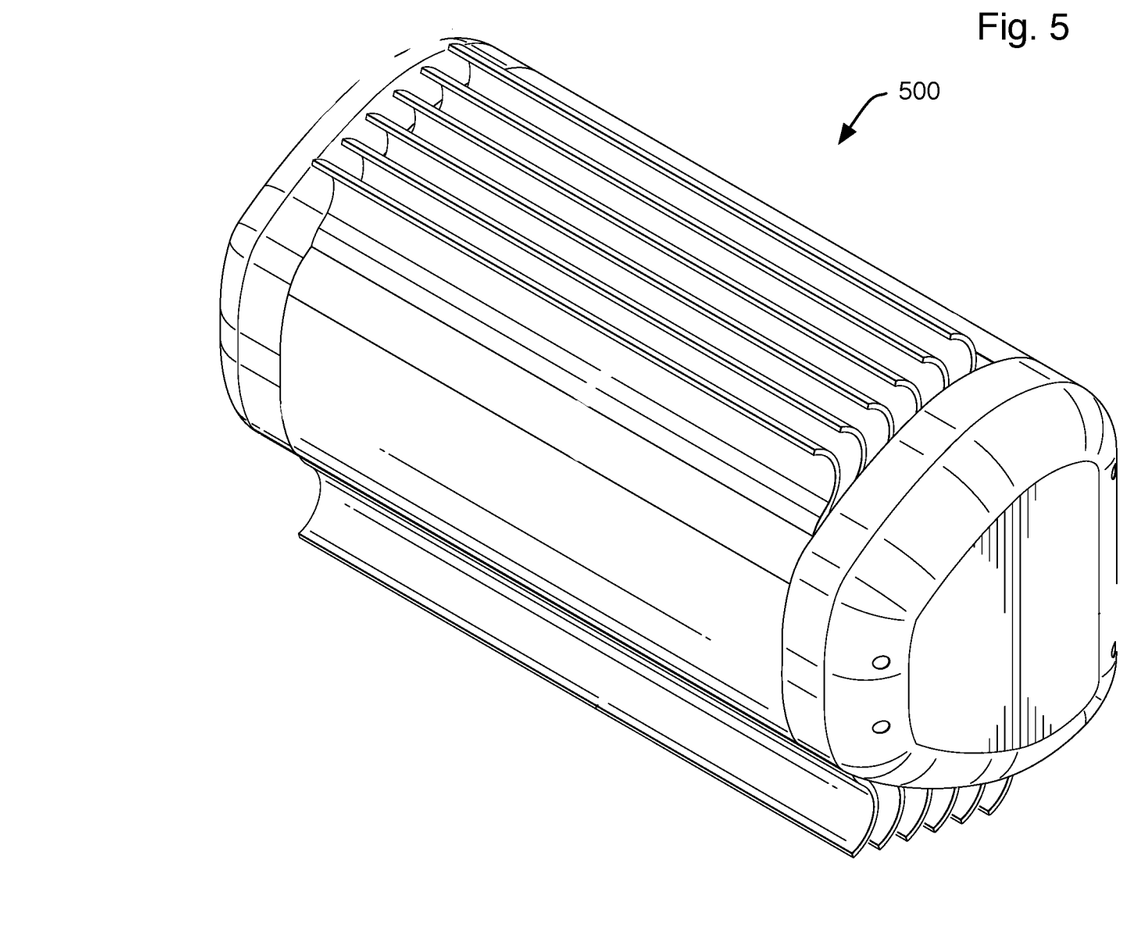
FIG. 5 is a perspective view of another example embodiment in which the present hybrid full-spectrum air purification may be employed for use with a mini-split system according to some embodiments.

FIG. 5 is a perspective view of another example embodiment 500 in which the present hybrid full-spectrum air purification may be employed for use with a mini-split system, or the like, according to some embodiments.

Figure 6:
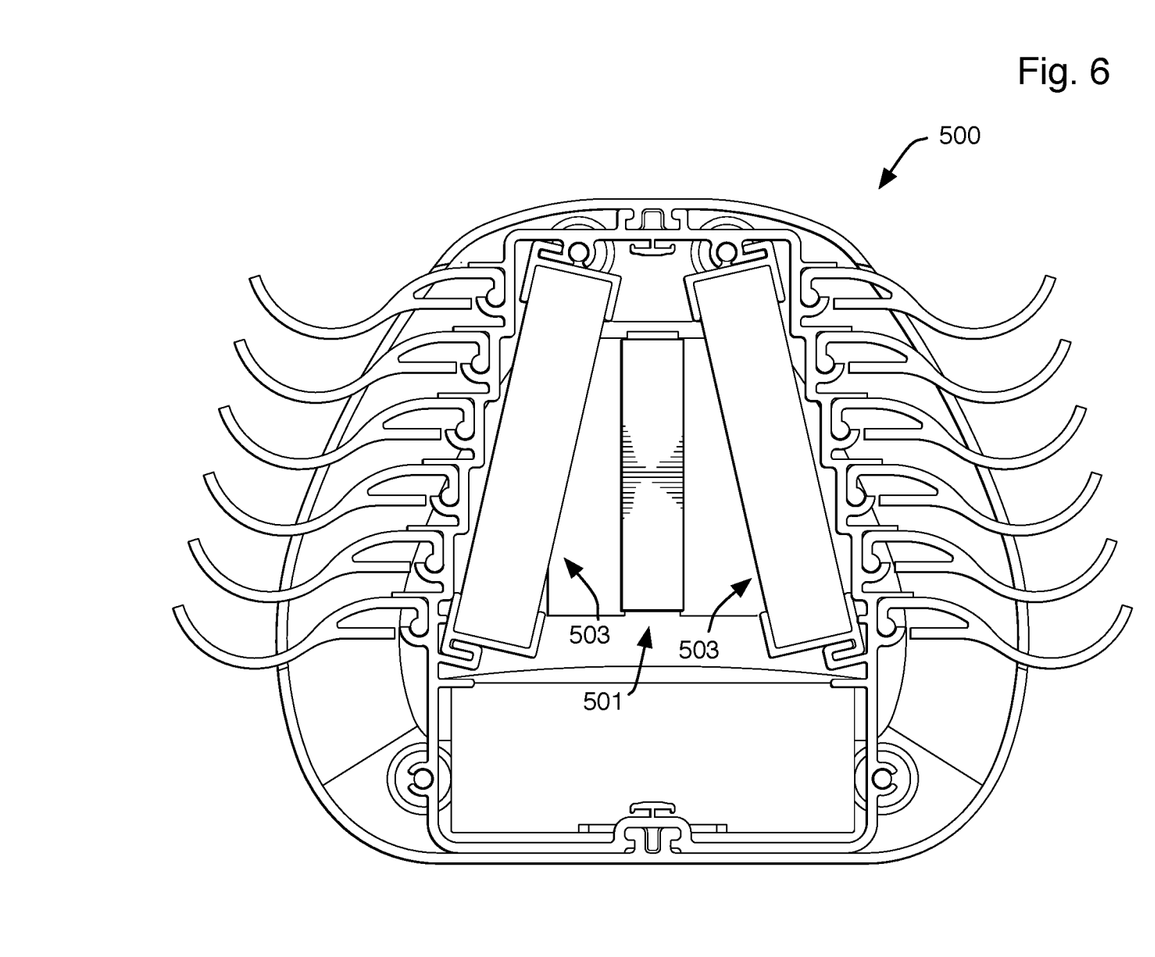
FIG. 6 is a fragmentary, generally cross-sectional, end view of an example hybrid full-spectrum air purifier device of FIG. 5 according to some embodiments.

FIG. 6 is a fragmentary, generally cross-sectional, end view of example hybrid full-spectrum air purifier device 500 of FIG. 5 according to some embodiments. FIG. 6 shows UV light source 501 and photocatalytic carbon monolith structures 503.

Figure 7:
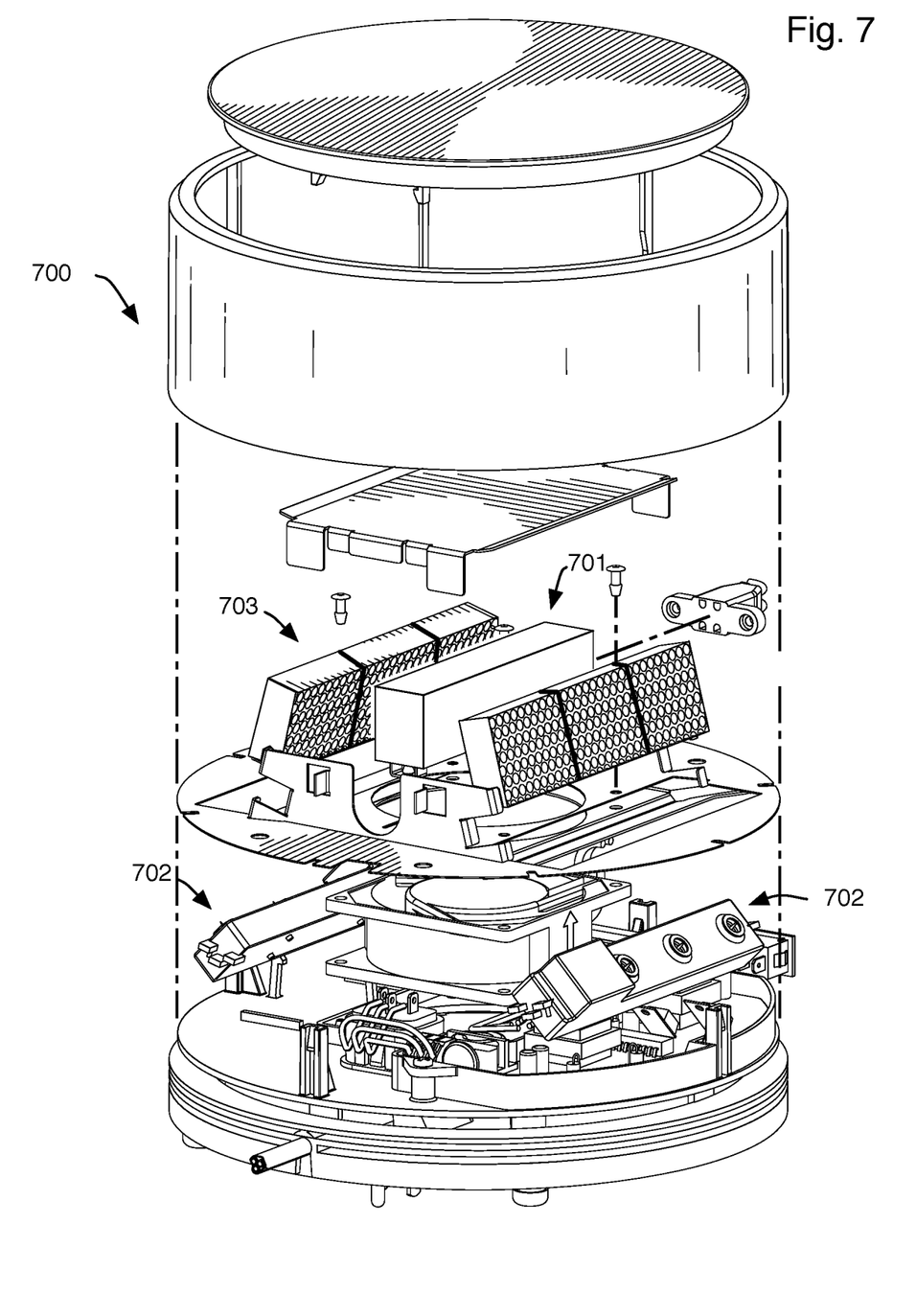
FIG. 7 is an exploded isometric view of a table-top or wall outlet mounted hybrid full-spectrum air purifier device according to some embodiments.

In another example, FIG. 7 is an exploded isometric view of table-top or wall outlet mounted hybrid full-spectrum air purifier device 700. FIG. 7 shows UV light source 701 ionizers 702 and photocatalytic carbon monolith structures 703.

Although the present embodiments and their advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

In one embodiment, a hybrid full spectrum air purification device comprises adsorbent volatile organic compound filters comprising at least one of zeolite, potassium permanganates, carbon, polymers, tris(hydroxymethyl)aminomethane, and/or tromethamine applied to one or more carbon monoliths or carbon monolith structures, and an ultraviolet light source disposed to provide ultraviolet light striking at least one face of the adsorbent volatile organic compound filters. The hybrid full spectrum air purification device may further comprise a means for providing ionization of air passing through the device. The ionization may be both negative and positive ionization, or may be either negative or positive ionization only. The adsorbent volatile organic compound filters may further comprise at least one room temperature bi-metallic nano-particle catalyst applied to the one or more carbon monoliths. The at least one room temperature bi-metallic nano-particle catalyst applied to the one or more carbon monoliths may comprise at least one supported noble metal based catalyst with at least one inert oxide. The at least one supported noble metal based catalyst applied to the one or more carbon monoliths may comprise platinum, palladium, gold, or silver. The at least one inert oxide applied to the one or more carbon monoliths with at least one supported noble metal based catalyst may comprise platinized tin oxide. The at least one room temperature bi-metallic nano-particle catalyst applied to the one or more carbon monoliths may comprise at least one non-noble metal oxide. The at least one non-noble metal oxide applied to the one or more carbon monoliths may comprise manganese dioxide or titanium dioxide. The hybrid full spectrum air purification device may be configured for installation immediately above, or adjacent, a temperature exchanger of an air ventilation, heating, and/or cooling system. The ultraviolet light source may comprise one or more light emitting diodes and/or an array of light emitting diodes. The ultraviolet light source may comprise one or more ultraviolet florescent lights.

In another embodiment, a method of air purification comprises passing air to be purified through a germicidal area, exposing the air to ultraviolet radiation provided by an ultraviolet light source of at least one wavelength, passing the air through at least one adsorbent volatile organic compound filter comprising one or more carbon monoliths having at least of zeolite, potassium permanganates, carbon, and/or polymers applied thereto, and exposing the air to ionization. The ionization may be both negative and positive ionization, or may be either negative or positive ionization only. The adsorbent volatile organic compound filters may further comprise at least one room temperature bi-metallic nano-particle catalyst applied to the one or more carbon monoliths. The at least one room temperature bi-metallic nano-particle catalyst applied to the one or more carbon monoliths comprise at least one supported noble metal based catalyst with at least one inert oxide. The at least one supported noble metal based catalyst applied to the one or more carbon monoliths may comprise platinum, palladium, gold, or silver. The at least one inert oxide applied to the one or more carbon monoliths with at least one supported noble metal based catalyst may comprise platinized tin oxide. The at least one room temperature bi-metallic nano-particle catalyst applied to the one or more carbon monoliths may comprise at least one non-noble metal oxide. The at least one non-noble metal oxide applied to the one or more carbon monoliths may comprise manganese dioxide or titanium dioxide. The method may use ultraviolet light sources comprising one or more light emitting diodes and/or an array of light emitting diodes and/or one or more ultraviolet florescent lights.

The method may further comprise installing a hybrid full spectrum air purification device immediately above, or adjacent, a temperature exchanger of an air ventilation, heating, and/or cooling system. The hybrid full spectrum air purification device may comprise the adsorbent volatile organic compound filters comprising at least one of zeolite, potassium permanganates, carbon, and/or polymers applied to one or more carbon monoliths. The ultraviolet light source may be disposed to provide ultraviolet light to strike at least one face of the adsorbent volatile organic compound filters. The device may comprise a means for providing the ionization to air passing through the device.

In a further embodiment, a method for manufacturing a hybrid full spectrum air purification device comprises applying at least one of zeolite, potassium permanganates, carbon, and/or polymers to one or more carbon monoliths to provide at least one adsorbent volatile organic compound filter, and disposing an ultraviolet light source with respect to the at least one adsorbent volatile organic compound carbon monolith filter to strike at least one face of the at least one adsorbent volatile organic compound carbon monolith filters. The method for manufacturing may further comprise disposing a means for providing ionization of air passing through the device with respect to the adsorbent volatile organic compound carbon monolith filter such that air exiting the adsorbent volatile organic compound carbon monolith filter is ionized. The means for providing ionization may be, for example, an ionizer or ion generator. The ionization may be both negative and positive ionization, or may be either negative or positive ionization only.

The method for manufacturing may further comprise applying at least one room temperature bi-metallic nano-particle catalyst to the one or more carbon monoliths. The at least one room temperature bi-metallic nano-particle catalyst applied to the one or more carbon monoliths may comprise at least one supported noble metal based catalyst with at least one inert oxide. The at least one supported noble metal based catalyst applied to the one or more carbon monoliths may comprise platinum, palladium, gold, or silver. The method at least one inert oxide applied to the one or more carbon monoliths with at least one supported noble metal based catalyst may comprise platinized tin oxide. The at least one room temperature bi-metallic nano-particle catalyst applied to the one or more carbon monoliths may comprise at least one non-noble metal oxide. The at least one non-noble metal oxide applied to the one or more carbon monoliths comprise manganese dioxide or titanium dioxide. The ultraviolet light source comprises one or more light emitting diodes and/or an array of light emitting diodes and/or one or more ultraviolet florescent lights.

The configuring the hybrid full spectrum air purification device for installation immediately above, or adjacent, a temperature exchanger of an air ventilation, heating, and/or cooling system.

The order in which each operation of a given method is performed may be changed, and various elements of the systems or devices illustrated herein may be added, reordered, combined, omitted, modified, etc. Various modifications and changes may be made as would be clear to a person of ordinary skill in the art having the benefit of this specification. It is intended that the inventions described herein embrace all such modifications and changes and, accordingly, the above description should be regarded in an illustrative rather than a restrictive sense.

The invention claimed is:

1. A hybrid full-spectrum air purification device, comprising:
    adsorbent volatile organic compound filters comprising tromethamine applied to one or more carbon monolith structures; and
    an ultraviolet light source disposed to provide ultraviolet light striking at least one face of the adsorbent volatile organic compound filters.

2. The hybrid full-spectrum air purification device of claim 1, further comprising means for providing ionization of air passing through the device.

3. The hybrid full-spectrum air purification device of claim 2, wherein the ionization is both negative and positive ionization.

4. The hybrid full-spectrum air purification device of claim 2, wherein the ionization is negative ionization only.

5. The hybrid full-spectrum air purification device of claim 1, wherein the adsorbent volatile organic compound filters further comprise at least one of zeolite, potassium permanganates, carbon, tris(hydroxymethyl)aminomethane, and polymers applied to the one or more carbon monolith structures.

6. The hybrid full-spectrum air purification device of claim 1, wherein the adsorbent volatile organic compound filters further comprise at least one room temperature bi-metallic nano-particle catalyst applied to the one or more carbon monolith structures.

7. The hybrid full-spectrum air purification device of claim 6, wherein the at least one room temperature bi-metallic nano-particle catalyst applied to the one or more carbon monolith structures comprises at least one supported noble metal based catalyst with at least one inert oxide.

8. The hybrid full-spectrum air purification device of claim 7, wherein the at least one supported noble metal based catalyst applied to the one or more carbon monolith structures comprises at least one of platinum, palladium, gold, and silver.

9. The hybrid full-spectrum air purification device of claim 7, wherein the at least one inert oxide applied to the one or more carbon monolith structures with the at least one supported noble metal based catalyst comprises platinized tin oxide.

10. The hybrid full-spectrum air purification device of claim 6, wherein the at least one room temperature bi-metallic nano-particle catalyst applied to the one or more carbon monolith structures comprises at least one non-noble metal oxide.

11. The hybrid full-spectrum air purification device of claim 10, wherein the at least one non-noble metal oxide applied to the one or more carbon monolith structures comprises at least one of manganese dioxide, and titanium dioxide.

12. The hybrid full-spectrum air purification device of claim 1, wherein the hybrid full-spectrum air purification device is configured for installation immediately above or adjacent to a temperature exchanger of an air ventilation, heating, and/or cooling system.

13. The hybrid full-spectrum air purification device of claim 1, wherein the ultraviolet light source comprises one or more light emitting diodes or an array of light emitting diodes.

14. The hybrid full-spectrum air purification device of claim 1, wherein the ultraviolet light source comprises one or more ultraviolet florescent lights.

15. A method of manufacture of a hybrid full-spectrum air purification device, comprising:

applying at least one of tromethamine to one or more carbon monoliths to provide at least one adsorbent volatile organic compound filter; and disposing an ultraviolet light source with respect to the at least one adsorbent volatile organic compound filter to strike at least one face of the at least one adsorbent volatile organic filter.

16. The method of claim 15, further comprising disposing means for providing ionization of air passing through the hybrid full-spectrum air purification device with respect to the at least one adsorbent volatile organic compound filter such that air exiting the at least one adsorbent volatile organic compound filter is ionized.

17. A method of air purification, comprising:

passing air to be purified through a germicidal area in which the air is exposed to ultraviolet radiation provided by an ultraviolet light source of at least one wavelength;

passing the air through at least one adsorbent volatile organic compound filter comprising one or more carbon monolith structures having tromethamine applied thereto; and exposing the air to ionization.

18. The method of claim 17, wherein the at least one adsorbent volatile organic compound filter further comprises at least one of zeolite, potassium permanganates, carbon, tris(hydroxymethyl)aminomethane, and polymers applied to the one or more carbon monolith structures.

19. The method of claim 17, wherein the at least one adsorbent volatile organic compound filter further comprises at least one room temperature bi-metallic nano-particle catalyst applied to the one or more carbon monolith structures.

20. The method of claim 17, further comprising:

exposing a temperature exchanger of an air ventilation, heating, and/or cooling system to the ultraviolet radiation provided by the ultraviolet light source.

* * * * *

UNITED STATES PATENT AND TRADEMARK OFFICE
CERTIFICATE OF CORRECTION

PATENT NO. : 10,814,030 B1  
APPLICATION NO. : 15/947335  
DATED : October 27, 2020  
INVENTOR(S) : Burnett et al.

Page 1 of 1

It is certified that error appears in the above-identified patent and that said Letters Patent is hereby corrected as shown below:

In the Claims

In Column 9, Line 1, Claim 15, delete "one of tromethamine" and insert -- tromethamine -- therefor.

Signed and Sealed this
Twenty-ninth Day of December, 2020

Andrei Iancu
*Director of the United States Patent and Trademark Office*